(12) United States Patent
Klatzmann (10) Patent No.: US 11,648,271 B2
(45) Date of Patent: May 16, 2023

(54) GENETICALLY MODIFIED T LYMPHOCYTES

(71) Applicant: David Klatzmann, Paris (FR)

(72) Inventor: David Klatzmann, Paris (FR)

(73) Assignee: David Klatzmann, Paris (FR)

( * ) Notice: Subject to any disclaimer, the term of this patent is extended or adjusted under 35 U.S.C. 154(b) by 455 days.

(21) Appl. No.: 16/312,497

(22) PCT Filed: Jun. 22, 2017

(86) PCT No.: PCT/EP2017/065330
§ 371 (c)(1),
(2) Date: Dec. 21, 2018

(87) PCT Pub. No.: WO2017/220704
PCT Pub. Date: Dec. 28, 2017

(65) Prior Publication Data
US 2019/0151364 A1 May 23, 2019

(30) Foreign Application Priority Data
Jun. 22, 2016 (EP) .................................... 16305756

(51) Int. Cl.
| | | |
|---|---|---|
| A61K 48/00 | (2006.01) | |
| C12N 15/63 | (2006.01) | |
| A61K 35/17 | (2015.01) | |
| C12N 5/0783 | (2010.01) | |
| A61P 31/00 | (2006.01) | |
| A61P 37/06 | (2006.01) | |
| A61P 29/00 | (2006.01) | |
| A61P 35/00 | (2006.01) | |
| C12N 15/86 | (2006.01) | |
| A01K 67/00 | (2006.01) | |
| A61K 39/00 | (2006.01) | |

(52) U.S. Cl.
CPC .............. *A61K 35/17* (2013.01); *A61P 29/00* (2018.01); *A61P 31/00* (2018.01); *A61P 35/00* (2018.01); *A61P 37/06* (2018.01); *C12N 5/0636* (2013.01); *C12N 5/0637* (2013.01); *C12N 15/86* (2013.01); *A61K 2039/5156* (2013.01); *C12N 2501/2302* (2013.01); *C12N 2510/00* (2013.01)

(58) Field of Classification Search
CPC . A61K 35/17; A61K 2039/5156; A61P 31/00; A61P 37/06; A61P 29/00; A61P 35/00; C12N 5/0636; C12N 5/0637; C12N 15/86; C12N 2501/2302; C12N 2510/00
See application file for complete search history.

(56) References Cited

U.S. PATENT DOCUMENTS

2004/0175357 A1* 9/2004 Shanafelt ............... C07K 14/55
424/85.2

OTHER PUBLICATIONS

Treisman, J., Hwu, P., Minamoto, S., Shafer, G. E., Cowherd, R., Morgan, R. A., & Rosenberg, S. A. (1995). Interleukin-2-transduced lymphocytes grow in an autocrine fashion and remain responsive to antigen. (Year: 1995).*
Markley, J. C., & Sadelain, M. (2010). IL-7 and IL-21 are superior to IL-2 and IL-15 in promoting human T cell-mediated rejection of systemic lymphoma in immunodeficient mice. Blood, The Journal of the American Society of Hematology, 115(17), 3508-3519. (Year: 2010).*
Kim, H., Peng, G., Hicks, J. M., Weiss, H. L., Van Meir, E. G., Brenner, M. K., & Yotnda, P. (2008). Engineering human tumor-specific cytotoxic T cells to function in a hypoxic environment. Molecular Therapy, 16(3), 599-606. (Year: 2008).*
Hsu, C., Abad, J. D., & Morgan, R. A. (2013). Characterization of human T lymphocytes engineered to express interleukin-15 and herpes simplex virus-thymidine kinase. journal of surgical research, 184(1), 282-289. (Year: 2013).*
Figueroa, J. A., Reidy, A., Mirandola, L., Trotter, K., Suvorava, N., Figueroa, A., . . . & Chiriva-Internati, M. (2015). Chimeric antigen receptor engineering: a right step in the evolution of adoptive cellular immunotherapy. International reviews of immunology, 34(2), 154-187. (Year: 2015).*
Cao J, Chen C, Zeng L, Li L, Li Z, Xu K. Engineered regulatory T cells prevent graft-versus-host disease while sparing the graft-versus-leukemia effect after bone marrow transplantation. Leukemia research. Oct. 1, 2010;34(10):1374-82. (Year: 2010).*
Di Ianni M, Falzetti F, Carotti A, Terenzi A, Castellino F, Bonifacio E, Del Papa B, Zei T, Ostini RI, Cecchini D, Aloisi T. Tregs prevent GVHD and promote immune reconstitution in HLA-haploidentical transplantation. Blood, The Journal of the American Society of Hematology. Apr. 7, 2011;117(14):3921-8. (Year: 2011).*
Kühl AA, Pawlowski NN, Grollich K, Blessenohl M, Westermann J, Zeitz M, Loddenkemper C, Hoffmann JC. Human peripheral γδ T cells possess regulatory potential. Immunology. Dec. 2009;128(4):580-8. (Year: 2009).*
Milojevic, D., Nguyen, K. D., Wara, D., & Mellins, E. D. (2008). Regulatory T cells and their role in rheumatic diseases: a potential target for novel therapeutic development. Pediatric Rheumatology, 6(1), 1-13. (Year: 2008).*
Zheng SG, Wang J, Wang P, Gray JD, Horwitz DA. IL-2 is essential for TGF-β to convert naive CD4+ CD25− cells to CD25+ Foxp3 + regulatory T cells and for expansion of these cells. The Journal of Immunology. Feb. 15, 2007;178(4):2018-27. (Year: 2007).*
Heemskerk B, Liu K, Dudley ME, Johnson LA, Kaiser A, Downey S, Zheng Z, Shelton TE, Matsuda K, Robbins PF, Morgan RA. Adoptive cell therapy for patients with melanoma, using tumor-infiltrating lymphocytes genetically engineered to secrete interleukin-2. Human gene therapy. May 1, 2008;19(5):496-510. (Year: 2008).*
Baine I, Basu S, Ames R, Sellers RS, Macian F. Helios induces epigenetic silencing of IL2 gene expression in regulatory T cells. The Journal of Immunology. Feb. 1, 2013;190(3):1008-16. (Year: 2013).*

(Continued)

*Primary Examiner* — Quang Nguyen
(74) *Attorney, Agent, or Firm* — McDermott Will & Emery LLP (57) ABSTRACT

The invention relates to a composition comprising regulatory T (Treg) cells or effector T cells (Teff) which stably express an interleukin selected from the group consisting of interleukin-2 (IL-2) or interleukin-15 (IL-15).

19 Claims, 8 Drawing Sheets
Specification includes a Sequence Listing.

(56) References Cited

OTHER PUBLICATIONS

Kim, Y. C., Zhang, A. H., Su, Y., Rieder, S. A., Rossi, R. J., Ettinger, R. A., . . . & Scott, D. W. (2015). Engineered antigen-specific human regulatory T cells: immunosuppression of FVIII-specific T-and B-cell responses. Blood, The Journal of the American Society of Hematology, 125(7), 1107-1115. (Year: 2015).*
Chen, Y. Y. (2015). Efficient gene editing in primary human T cells. Trends in immunology, 36(11), 667-669. (Year: 2015).*
Kurose K, Ohue Y, Sato E, Yamauchi A, Eikawa S, Isobe M, Nishio Y, Uenaka A, Oka M, Nakayama E. Increase in activated Treg in TIL in lung cancer and in vitro depletion of Treg by ADCC using an antihuman CCR4 mAb (KM2760). Journal of Thoracic Oncology. Jan. 1, 2015;10(1):74-83. (Year: 2015).*
Georgoudaki, A. M., Sutlu, T., & Alici, E. (2010). Suicide gene therapy for graft-versus-host disease. Immunotherapy, 2(4), 521-537 (Year: 2010).*
Quintarelli, C., Vera, J. F., Savoldo, B., et al. (2007). Co-expression of cytokine and suicide genes to enhance the activity and safety of tumor-specific cytotoxic T lymphocytes. Blood, The Journal of the American Society of Hematology, 110(8), 2793-2802. (Year: 2007).*
Kovacsovics-Bankowski, M., Chisholm, L., Vercellini, J., et al. (2014). Detailed characterization of tumor infiltrating lymphocytes in two distinct human solid malignancies show phenotypic similarities. Journal for immunotherapy of cancer, 2(1), 1-12. (Year: 2014).*
Markley JC, Sadelain M. IL-7 and IL-21 are superior to IL-2 and IL-15 in promoting human T cell-mediated rejection of systemic lymphoma in immunodeficient mice. Blood, The Journal of the American Society of Hematology. Apr. 29, 2010;115(17):3508-19; cited in prior Office action. (dated 2010).*
Heemskerk B, Liu K, Dudley ME, Johnson LA, et al. Adoptive cell therapy for patients with melanoma, using tumor-infiltrating lymphocytes genetically engineered to secrete interleukin-2. Human gene therapy. May 1, 2008;19(5):496-510; cited in prior Office action. (dated 2008).*
Milojevic, D., Nguyen, K. D., Wara, D., & Mellins, E. D. (2008). Regulatory T cells and their role in rheumatic diseases: a potential target for novel therapeutic development. Pediatric Rheumatology, 6(1), 1-13; cited in prior Office action. (dated 2008).*
Kovacsovics-Bankowski, M., Chisholm, L., Vercellini, J., et al. (2014). Detailed characterization of tumor infiltrating lymphocytes in two distinct human solid malignancies show phenotypic similarities. Journal for immunotherapy of cancer, 2(1), 1-12; cited in prior Office action. (dated 2014).*
Figueroa JA, Reidy A, Mirandola L, Trotter K, et al. Chimeric antigen receptor engineering: a right step in the evolution of adoptive cellular immunotherapy. International reviews of immunology. Mar. 4, 2015;34(2):154-87; cited in a prior Office action. (dated 2015).*
McKee MD, Fichera A, Nishimura MI. T cell immunotherapy. Front Biosci. Jan. 1, 2007;12:919-32. (Year: 2007).*
Wright GP, Notley CA, Xue SA, Bendle GM, Holler A, Schumacher TN, Ehrenstein MR, Stauss HJ. Adoptive therapy with redirected primary regulatory T cells results in antigen-specific suppression of arthritis. Proceedings of the National Academy of Sciences. Nov. 10, 2009;106(45):19078-83. (Year: 2009).*
Haque R, Lei F, Xiong X, Bian Y, Zhao B, Wu Y, Song J. Programming of regulatory T cells from pluripotent stem cells and prevention of autoimmunity. The Journal of Immunology. Aug. 1, 2012;189(3):1228-36. (Year: 2012).*
Fan H, Cao P, Game DS, Dazzi F, Liu Z, Jiang S. Regulatory T cell therapy for the induction of clinical organ transplantation tolerance. InSeminars in immunology Dec. 1, 2011 (vol. 23, No. 6, pp. 453-461). Academic Press. (Year: 2011).*
Kafri T, Van Praag H, Gage FH, Verma IM. Lentiviral vectors: regulated gene expression. Molecular Therapy. Jun. 1, 2000;1(6):516-21. (Year: 2000).*
Marin V, Cribioli E, Philip B, Tettamanti S, Pizzitola I, Biondi A, Biagi E, Pule M. Comparison of different suicide-gene strategies for the safety improvement of genetically manipulated T cells. Human gene therapy methods. Dec. 1, 2012;23(6):376-86. (Year: 2012).*
Jethwa H, Adami AA, Maher J. Use of gene-modified regulatory T-cells to control autoimmune and alloimmune pathology: is now the right time? Clinical Immunology. Jan. 1, 2014;150(1):51-63. (Year: 2014).*
Chen, Y. Y. (2015). Efficient gene editing in primary human T cells. Trends in immunology, 36(11), 667-669; cited in prior Office action. (dated 2015).*
Kurose K, Ohue Y, Sato E, Yamauchi A, Eikawa S, et al. Increase in activated Treg in TIL in lung cancer and in vitro depletion of Treg by ADCC using an antihuman CCR4 mAb (KM2760). Journal of Thoracic Oncology. Jan. 1, 2015;10(1):74-83; cited in prior Office action (dated 2015).*
Jensen MC, Riddell SR. Designing chimeric antigen receptors to effectively and safely target tumors. Current opinion in immunology. Apr. 1, 2015;33:9-15. (Year: 2015).*
Barrett DM, Grupp SA, June CH. Chimeric antigen receptor-and TCR-modified T cells enter main street and wall street. The Journal of Immunology. Aug. 1, 2015;195(3):755-61 (Year: 2015).*
Georgoudaki, A. M., Sutlu, T., & Alici, E. (2010). Suicide gene therapy for graft-versus-host disease. Immunotherapy, 2(4), 521-537; cited in prior Office action (dated 2010).*
Quintarelli, C., Vera, J. F., Savoldo, B., et al. (2007). Co-expression of cytokine and suicide genes to enhance the activity and safety of tumor-specific cytotoxic T lymphocytes. Blood, The Journal of the American Society of Hematology, 110(8), 2793-2802; cited in prior Office action. (dated 2007).*

* cited by examiner

FIG. 3A  Teffs

FIG. 3B  Tregs alone

Fold change of the % of GFP+ cells
Among the adoptively transferred cells

FIG. 4C

Fold change of the absolute number of GFP+ cells
among the adoptively transferred cells

SEQUENCE LISTING

```
<160> NUMBER OF SEQ ID NOS: 5

<210> SEQ ID NO 1
<211> LENGTH: 822
<212> TYPE: DNA
<213> ORGANISM: Homo sapiens
<220> FEATURE:
<221> NAME/KEY: CDS
<222> LOCATION: (56)..(517)

<400> SEQUENCE: 1
agttccctat cactctcttt aatcactact cacagtaacc tcaactcctg ccaca atg      58
                                                              Met
                                                              1 tac agg atg caa ctc ctg tct tgc att gca cta agt ctt gca ctt gtc     106
Tyr Arg Met Gln Leu Leu Ser Cys Ile Ala Leu Ser Leu Ala Leu Val
         5                  10                  15 aca aac agt gca cct act tca agt tct aca aag aaa aca cag cta caa     154
Thr Asn Ser Ala Pro Thr Ser Ser Ser Thr Lys Lys Thr Gln Leu Gln
     20                  25                  30 ctg gag cat tta ctg ctg gat tta cag atg att ttg aat gga att aat     202
Leu Glu His Leu Leu Leu Asp Leu Gln Met Ile Leu Asn Gly Ile Asn
 35                  40                  45 aat tac aag aat ccc aaa ctc acc agg atg ctc aca ttt aag ttt tac     250
Asn Tyr Lys Asn Pro Lys Leu Thr Arg Met Leu Thr Phe Lys Phe Tyr
 50                  55                  60                  65 atg ccc aag aag gcc aca gaa ctg aaa cat ctt cag tgt cta gaa gaa     298
Met Pro Lys Lys Ala Thr Glu Leu Lys His Leu Gln Cys Leu Glu Glu
                 70                  75                  80 gaa ctc aaa cct ctg gag gaa gtg cta aat tta gct caa agc aaa aac     346
Glu Leu Lys Pro Leu Glu Glu Val Leu Asn Leu Ala Gln Ser Lys Asn
             85                  90                  95 ttt cac tta aga ccc agg gac tta atc agc aat atc aac gta ata gtt     394
Phe His Leu Arg Pro Arg Asp Leu Ile Ser Asn Ile Asn Val Ile Val
         100                 105                 110
```

```
ctg gaa cta aag gga tct gaa aca aca ttc atg tgt gaa tat gct gat    442
Leu Glu Leu Lys Gly Ser Glu Thr Thr Phe Met Cys Glu Tyr Ala Asp
    115                 120                 125 gag aca gca acc att gta gaa ttt ctg aac aga tgg att acc ttt tgt    490
Glu Thr Ala Thr Ile Val Glu Phe Leu Asn Arg Trp Ile Thr Phe Cys
130                 135                 140                 145 caa agc atc atc tca aca ctg act tga taattaagtg cttcccactt          537
Gln Ser Ile Ile Ser Thr Leu Thr
                150 aaaacatatc aggccttcta tttatttaaa tatttaaatt ttatatttat tgttgaatgt  597 atggtttgct acctattgta actattattc ttaatcttaa aactataaat atggatcttt  657 tatgattctt tttgtaagcc ctaggggctc taaaatggtt tcacttattt atcccaaaat  717 atttattatt atgttgaatg ttaaatatag tatctatgta gattggttag taaaactatt  777 taataaattt gataaatata aaaaaaaaaa aaaaaaaaaa aaaaa                  822

<210> SEQ ID NO 2
<211> LENGTH: 153
<212> TYPE: PRT
<213> ORGANISM: Homo sapiens

<400> SEQUENCE: 2

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 3
<211> LENGTH: 133
<212> TYPE: PRT
<213> ORGANISM: Homo sapiens

<400> SEQUENCE: 3

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60
```

```
Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

```
<210> SEQ ID NO 4
<211> LENGTH: 486
<212> TYPE: DNA
<213> ORGANISM: Homo sapiens
<220> FEATURE:
<221> NAME/KEY: CDS
<222> LOCATION: (57)..(467)

<400> SEQUENCE: 4
cggattggga tcggacctac ttgattcact tctgggaaat caaggatcta cgtacc atg      59
                                                                 Met
                                                                  1 gat ttt cag gtg cag att ttc agc ttc ctg cta atc agt gcc tca gtc     107
Asp Phe Gln Val Gln Ile Phe Ser Phe Leu Leu Ile Ser Ala Ser Val
          5                  10                  15 ata atg tct aga gcc aac tgg gtg aat gta ata agt gat ttg aaa aaa     155
Ile Met Ser Arg Ala Asn Trp Val Asn Val Ile Ser Asp Leu Lys Lys
         20                  25                  30 att gaa gat ctt att caa tct atg cat att gat gct act tta tat acg     203
Ile Glu Asp Leu Ile Gln Ser Met His Ile Asp Ala Thr Leu Tyr Thr
 35                  40                  45 gaa agt gat gtt cac ccc agt tgc aaa gta aca gca atg aag tgc ttt     251
Glu Ser Asp Val His Pro Ser Cys Lys Val Thr Ala Met Lys Cys Phe
 50                  55                  60                  65 ctc ttg gag tta caa gtt att tca ctt gag tcc gga gat gca agt att     299
Leu Leu Glu Leu Gln Val Ile Ser Leu Glu Ser Gly Asp Ala Ser Ile
             70                  75                  80 cat gat aca gta gaa aat ctg atc atc cta gca aac aac agt ttg tct     347
His Asp Thr Val Glu Asn Leu Ile Ile Leu Ala Asn Asn Ser Leu Ser
             85                  90                  95 tct aat ggg aat gta aca gaa tct gga tgc aaa gaa tgt gag gaa ctg     395
Ser Asn Gly Asn Val Thr Glu Ser Gly Cys Lys Glu Cys Glu Glu Leu
        100                 105                 110 gag gaa aaa aat att aaa gaa ttt ttg cag agt ttt gta cat att gtc     443
Glu Glu Lys Asn Ile Lys Glu Phe Leu Gln Ser Phe Val His Ile Val
        115                 120                 125 caa atg ttc atc aac act tct tga ttgcaattga ttcctcgag                486
Gln Met Phe Ile Asn Thr Ser
130                 135
```

```
<210> SEQ ID NO 5
<211> LENGTH: 136
<212> TYPE: PRT
<213> ORGANISM: Homo sapiens

<400> SEQUENCE: 5

Met Asp Phe Gln Val Gln Ile Phe Ser Phe Leu Leu Ile Ser Ala Ser
  1               5                  10                  15

Val Ile Met Ser Arg Ala Asn Trp Val Asn Val Ile Ser Asp Leu Lys
             20                  25                  30
```

-continued

```
Lys Ile Glu Asp Leu Ile Gln Ser Met His Ile Asp Ala Thr Leu Tyr
         35                  40                  45

Thr Glu Ser Asp Val His Pro Ser Cys Lys Val Thr Ala Met Lys Cys
         50                  55                  60

Phe Leu Leu Glu Leu Gln Val Ile Ser Leu Glu Ser Gly Asp Ala Ser
 65              70                  75                  80

Ile His Asp Thr Val Glu Asn Leu Ile Ile Leu Ala Asn Asn Ser Leu
                 85                  90                  95

Ser Ser Asn Gly Asn Val Thr Glu Ser Gly Cys Lys Glu Cys Glu Glu
             100                 105                 110

Leu Glu Glu Lys Asn Ile Lys Glu Phe Leu Gln Ser Phe Val His Ile
         115                 120                 125

Val Gln Met Phe Ile Asn Thr Ser
    130                 135
```

GENETICALLY MODIFIED T LYMPHOCYTES

CROSS-REFERENCE TO RELATED APPLICATIONS

This Application is a national stage filing under 35 U.S.C. § 371 of International Patent Application Serial No. PCT/EP2017/065330, filed Jun. 22, 2017, which claims the benefit of priority to European Patent Application Serial Number 16305756.5, filed Jun. 22, 2016, the entire contents of each of which are incorporated by reference herein.

SEQUENCE LISTING

The instant application contains a Sequence Listing which has been filed electronically in ASCII format and is hereby incorporated by reference in its entirety. Said ASCII copy, created on May 24, 2021, is named 112360-0020-70017US00.txt and is 10,000 bytes in size.

The present invention relates to the field of cell therapy. The invention provides a composition comprising regulatory T (Treg) cells or effector T cells (Teff) which stably express an interleukin selected from the group consisting of interleukin-2 (IL-2) or interleukin-15 (IL-15). Such modified Treg compositions are useful in treating or preventing diseases with an immune component, e.g. autoimmune and/or inflammatory diseases, allergies, transplant rejection or Graft versus Host Disease (GVHD). Modified Teff compositions are useful in treating cancers and infections.

BACKGROUND OF THE INVENTION

IL-2 is a drug initially described to support the activation and function of Teffs. Likewise, IL-2 has been used at high dose for cancer immunotherapy. At these high doses, IL-2 activates Teffs.

It was recently showed that regulatory cells (Tregs) are dependent on interleukin 2 (IL-2) for their development, function and survival (Klatzmann and Abbas, 2015, Nat Rev Immunol. 15(5):283-94). Knockout of the gene encoding IL-2 in mice led to severe lymphoproliferation and autoimmunity, rather than the predicted immune deficiency. This finding was soon followed by the description of similar phenotypes of mice with a knockout of the gene encoding the β-chain of the IL-2 receptor (IL-2Rβ; also referred to as CD122) or IL-2Rα (also referred to as CD25). The description of CD25 as the canonical phenotypic marker of Tregs suggested that IL-2 signalling defects might affect Tregs and lead to autoimmunity. This was confirmed by showing that Tregs are absent in IL-2-deficient or IL-2R-deficient mice, and that adoptive transfer of these cells from normal mice could prevent autoimmunity in the deficient mice. The conclusion of these knockout mouse studies is that the dominant role of IL-2 is the maintenance of Tregs, and not the development of effector and memory T cells, because loss of IL-2 signalling leads to a breakdown of immune tolerance and homeostasis.

However, Tregs intrinsically cannot produce IL-2, which is provided primarily by the non-Tregs activated T cells. In fact, during immune responses the activated Teffs "boost" Tregs in a regulatory loop (Grinberg-Bleyer et al, 2010, J Clin Invest, 120(12):4558-68). When the effector immune response tends to decrease, the Tregs may not find enough IL2 to be efficient.

Tregs control autoimmune diseases and inflammation, and regulate all immune responses. Thus, Tregs based therapy has great potential for the treatment of autoimmune and/or inflammatory diseases, or allergies (Klatzmann & Abbas, supra). This could be achieved by expanding and activating Tregs in vivo, for example by low dose IL2 (Klatzmann & Abbas, supra). This can also be achieved by cell therapy with ex vivo expanded Tregs (Gitelman and Bluestone, 2016, J Autoimmun. 71:78-87), including naturally occurring or modified Tregs. However, this may require repeated injections of large amounts of Tregs, which could be cumbersome.

Teff based therapies have also been developed notably in the field of cancer. Such therapies can involve either naturally occurring anti-cancer Teffs, as those that can be harvested from "tumor infiltrating lymphocytes (TIL), or artificial Teffs such as CAR-T cells (Feldman et al, 2015 Semin Oncol. 42(4):626-39).

Culturing Tregs and Teffs involves adding large amounts of IL-2 to the culture medium. After days or weeks of culture with IL-2, these cells are re-injected in patients who represent a relatively IL-2 deprived environment compared to these culture conditions, and specially for patients with autoimmune diseases who often have a genetically controlled lower IL-2 production that normal individuals (Klatzmann and Abbas, supra). This may affect Tregs and Teffs survival and function.

There is thus a need for improved T cell therapies.

SUMMARY OF THE INVENTION

The invention provides regulatory T (Treg) cells or effector T cells (Teff) which stably express an interleukin selected from the group consisting of interleukin-2 (IL-2) or interleukin-15 (IL-15).

A subject of the present invention is a composition comprising Tregs or Teffs.

Tregs which secrete IL-2 are even more preferred.

In a preferred embodiment, the cells have been genetically modified to stably express said interleukin in a constitutive manner.

In another embodiment, the cells have been genetically modified to stably express said interleukin in an inducible manner.

In a preferred aspect, the cells have been modified to express a transgene encoding said interleukin and a suicide gene, which transgene and suicide genes integrate the genome of the cells.

In a preferred aspect, the cells have been modified by an integrative viral vector, which is preferably a lentivirus vector. In another aspect, the cells have been modified by a system that allows integration of transgenes, such as Crspr-Cas9 system, Zing finger nucleases, TALENs or meganucleases.

LEGENDS TO THE FIGURES

FIG. 1 is a map of the "hIL-2-2A-CD-2A-GFP" vector. This modified lentiviral plasmid pBL249 has a self-inactivating retroviral genome, contains a hIL-2 transgene associated with a suicide gene (cytosine deaminase (CD)) and a reporter gene (Green Fluorescent Protein (GFP)). All transgene expression is under an EF1 alpha promoter. The three transgenes are linked by "2A" sequences and are thus expressed from a single RNA. Peptide intermediate sequences 2A cause ribosomal jump to next start codon of the mRNA, allowing for co-expression of all transgene from the single RNA. The GFP gene expressed by this vector is for the purpose of facilitating the follow-up of the experiment. It can be advantageously replaced by any transgene of interest and notably by targeting moieties such as CARs or by genes participating to the Treg suppression, such as IL-10 or TGF-beta.

In FIG. 2D, surviving Tregs that produce only GFP ($Treg_{GFP}$) (middle panel) express less Foxp3 and CD25 than the control fresh Tregs (left panel). In contrast, Tregs that produce IL-2 ($Treg_{IL2}$) express even higher levels of FoxP3 and CD25 compared to control fresh Tregs indicating that they are activated. In FIG. 2E, control fresh Tregs or Tregs that produce only GFP do not express pSTAT5, which is induced by the interaction of IL-2 with the IL-2R. In contrast, Tregs that produce IL-2 express high levels of pSTAT5 further indicating that they are highly activated. Altogether, FIGS. 2A to 2E demonstrate that Treg transduced to produce endogenous IL-2 are IL-2 sufficient in vitro and are activated.

FIGS. 3A to 3C show the suppressive activity of Tregs producing endogenous IL-2. CD4+ Effector T cells (Teffs) are incubated with a dye that is diluted during cell division. Upon activation, they lost this dye (FIG. 3A) indicating their division. Tregs that have not been stained with dye are shown (FIG. 3B). When Teffs are mixed with $Treg_{IL2}$ cultured in the absence of IL-2, at the indicated ratios, there is a dose-dependent inhibition of Teffs division. At the highest ratios, the inhibition is complete, and the proliferation of Teffs starts to reappear at the 1/8 ratio (FIG. 3C). This shows that $Treg_{IL2}$ grown in the absence of IL-2 are highly suppressive.

FIGS. 4B and C show the variation of proportion (FIG. 4B) and number (FIG. 4C) of the transduced cells adoptively transferred to recipient mice devoid of T cells. The transferred human cells are first identified and counted, and the proportion of cells expressing GFP within these cells is then determined. The proportion of transduced cells that express only GFP ($Treg_{GFP}$) remains stable, while the proportion of $Treg_{IL2}$ continuously increase over time (FIG. 4B). This is also true in term of numbers (FIG. 4C). The number of $Treg_{GFP}$ continuously declines, while the numbers of $Treg_{IL2}$ continuously increase up until day-35, and then decline. Results are from the mean±SEM of 6 mice for $Treg_{GFP}$ and 7 mice for $Treg_{IL2}$. Non-parametric Mann Whitney test shows a strong significance with $p<0.01$ for FIGS. 4B and 4C.

FIGS. 5A and 5B show the phenotype of the human Tregs injected in mice lacking T cells. $Treg_{IL}2$ and $Treg_{GFP}$ have been adoptively transferred to mice that lack T cells and thus have no (or very little) IL-2 in their environment. The injected cell population has not been purified and thus represent a mix of transduced (approximately 20%) and non-transduced cells. At day 14 post injection, the injected cells are first analyzed by the expression of the human CD45 markers (FIG. 5A, left panels). The CD45+ cells are more numerous for the $Treg_{IL2}$ (lower panel) than for the $Treg_{GFP}$ (upper panel). The expression of CD25 and Foxp3 are then looked at in these cells (FIG. 5A, right panels). Most of the few surviving $Treg_{GFP}$ still express CD25 and Foxp3, but seemingly at low levels. The more numerous $Treg_{IL2}$ also express CD25 and Foxp3 at high levels. The higher intensity of CD25 expression (FIG. 5B, left panel) and of FoxP3 expression (FIG. 5B, right panel) in $Treg_{IL2}$ than in $Treg_{GFP}$ is shown as histograms. FIG. 5C reports the same results than FIG. 5A, and shows an even more pronounced difference in the number of surviving cells which is much higher for $Treg_{IL2}$ (lower panels) than for $Treg_{GFP}$ (higher panels). FIG. 5D shows the presence of the adoptively transferred cells in different tissues. $Treg_{GFP}$ are at low numbers in tissues, while $Treg_{IL2}$ at detected in high numbers in spleen, liver and lung. In all cases they express high levels of CD25 and Foxp3.

FIGS. 7A and 7B show the higher efficiency of Teff expressing IL-2 ($Teff_{IL2}$) 1 in a model of experimental graft versus host disease (GVHD). NSG mice that lack T cells are adoptively transferred with $Teff_{GFP}$ alone or $Teff_{IL2}$. While control mice that have not received Teff gain weight, mice adoptively transferred with Teffs lost weight starting at 3 weeks. Mice that have received $Teff_{IL2}$ lost more weight than those having received $Teff_{GFP}$ (FIG. 7A). The T cell infiltration of the liver is much more pronounced for mice having received $Teff_{IL2}$ than those having received $Teff_{GFP}$, indicating a more pronounced GVHD.

DETAILED DESCRIPTION OF THE INVENTION

The inventor made the hypothesis that a T cell therapy could be improved by using Tregs or Teffs with improved properties in terms of survival and function.

In that prospect, the inventor proposes to use Tregs or Teffs that stably express the gene coding for IL-2 (or for IL-15) would support their survival and function in the absence of IL-2. According to the invention, by secreting IL-2 or IL-15, such Tregs or Teffs may have a survival advantage and/or a potentiation of their suppressive activity in vivo. This may concern the transduced cells themselves, in an autocrine manner, and neighboring bystander cells in an exocrine manner.

Definitions

A "stable transduction" or "stable expression" of a transgene means that the transgene is integrated into the cells' genome. The hallmark of stably transduced cells is that the foreign gene becomes part of the genome and is therefore replicated. Descendants of these transduced cells, therefore, will also express the new gene.

"Regulatory T cells" or "Tregs" are T lymphocytes having immunosuppressive activity. Natural Tregs are usually characterized as CD4+CD25+Foxp3+ cells, preferably CD127 (low),CD4+,CD25(high),Foxp3+ cells. Tregs play a major role in the control of inflammatory diseases, although their mode of action in such disease is not fully understood. In fact, in most inflammatory diseases, Treg depletion exacerbates disease while Treg addition decreases it. Most Tregs are CD4+ cells, although there also exists a rare population of CD8+Foxp3+T lymphocytes with a suppressive activity.

Within the context of this application, the term "effector T cells" (or "Teffs") designates conventional T lymphocytes other than Tregs (sometimes also referred to as Tconv in the literature), which express one or more T cell receptor (TCR) and perform effector functions (e.g., cytotoxic activity, cytokine secretion, anti-self recognition, etc). Major populations of human Teff according to this invention include CD4+T helper lymphocytes (e.g., Th0, Th1, Th9, Th17) and CD4+ or CD8+ cytotoxic T lymphocytes, and they can be specific for self or non-self antigens.

Within the context of this invention, the term "IL-2" designates any source of IL-2, including mammalian sources such as e.g., human, mouse, rat, primate, and pig, and may be native or an active variant of the native IL-2 polypeptide. A nucleotide and an amino acid sequence of human IL-2 are disclosed, for instance, in Genbank access number NM_000586. The invention more preferably uses a human IL-2. A nucleotide sequence of hIL-2 is provided as SEQ ID NO:1, the corresponding amino acid sequence is SEQ ID NO: 2. The signal peptide is amino acids 1-20 of SEQ ID NO:2, the mature peptide (starting with an alanine at position 21 of SEQ ID NO:2) is shown as SEQ ID NO; 3. Active variants of IL-2 have been disclosed in the literature. Variants of the native IL-2 can be fragments, analogues, and derivatives thereof. Some of the variants may have improved activity towards Tregs or Teffs, and would thus be preferably used in those cells. By "fragment" is intended a polypeptide comprising only a part of the intact polypeptide sequence. An "analogue" designates a polypeptide comprising the native polypeptide sequence with one or more amino acid substitutions, insertions, or deletions. Active variants of a reference IL-2 polypeptide generally have at least 75%, preferably at least 85%, more preferably at least 90% amino acid sequence identity to the amino acid sequence of the reference IL-2 polypeptide. Methods for determining whether a variant IL-2 polypeptide is active are available in the art and are specifically described in the present invention. An active variant is, most preferably, a variant that activates Tregs. Examples of IL-2 variants are disclosed, for instance, in patents or patent applications EP109748, EP136489, U.S. Pat. No. 4,752,585; EP200280, or EP118617, as well as in U.S. Pat. No. 6,348,192, WO99/60128, EP2970423, WO16/164937. In a preferred embodiment, the IL-2 variant protein shows C125S substitution, still preferably it is des-alanyl-1, serine-125 human interleukin-2 (referring to mature human IL-2 peptide shown as SEQ ID NO:3). In another preferred embodiment, the IL-2 variant protein comprises human IL-2 with a substitution selected from the group consisting of L12G, L12K, L12Q, L125, Q.13G, E15A, E15G, E155, H16A, H16D, H16G, H16K, H16M, H16N, H16R, H16S, H16T, H16V, H16Y, L19A, L19D, L19E, L19G, L19N, L19R, L19S, L19T, L19V, D20A, D20E, D20F, D20G, D20H, D20T, D20W, M23R, R81A, R81G, R81S, R81T, D84A, D84E, D84G, D84I, D84M, D84Q D84R, D84S, D84T, S87R, N88A, N88D, N88E, N88F, N88I, N88G, N88M, N88R, N88S, N88V, N88W, V91D, V91E, V91G, V91S, V91K, 192K, 192R, and E95G, as well as D109C, Q126L, Q126F, still preferably consisting of N88R, N88I, N88G, D20H, D109C, Q126L, Q126F, D84G, or D84I relative to human mature IL2 protein (SEQ ID NO: 3). Active variants that have a better selectivity for Tregs than wild-type IL-2 are preferred for use in Tregs, while active variants that have a better selectivity better than wild-type IL-2 for Teffs are preferred for use in Teffs.

IL-15 is a cytokine that is structurally similar to IL-2. Within the context of this invention, the term "IL-15" designates any source of IL-15, including mammalian sources such as e.g., human, mouse, rat, primate, and pig, and may be native or an active variant of the native IL-15 polypeptide. A nucleotide and an amino acid sequence of human IL-2 is disclosed, for instance, in Genbank access number Y09908. A nucleotide sequence of hIL-15 is provided as SEQ ID NO:4. The corresponding amino acid sequence is SEQ ID NO:5. The invention more preferably uses a human IL-15. Variants of the native IL-15 can be fragments, analogues, and derivatives thereof. By "fragment" is intended a polypeptide comprising only a part of the intact polypeptide sequence. An "analogue" designates a polypeptide comprising the native polypeptide sequence with one or more amino acid substitutions, insertions, or deletions. Active variants of a reference IL-2 polypeptide generally have at least 75%, preferably at least 85%, more preferably at least 90% amino acid sequence identity to the amino acid sequence of the reference IL-2 polypeptide. Methods for determining whether a variant IL-15 polypeptide is active are available in the art and are specifically described in the present invention. An active variant is, most preferably, a variant that activates Tregs. Like IL-2, IL-15 binds to and signals through a complex composed of the IL-2/IL-15 receptor beta chain. IL-15 induces a T-cell activation and proliferation in particular of CD8+ T-cells and also provides survival signals to maintain memory cells in the absence of antigens, favored CD8+ T-cells and activates monocytes.

The T lymphocytes express a "molecule allowing their specific destruction". This may be a molecule encoded by a transgene or a molecule that is naturally expressed by the T lymphocytes, when the latter are allogenic. The term "specific destruction" means that only the T lymphocytes administered to the patient will be destroyed, to prevent the development of a GVH reaction or stop any adverse reaction due to the injected cells. The "molecule allowing their specific destruction" may be for example an antigen of the HLA system, the molecules Thy-1, NGF receptor or a truncated form of the receptor, or an antigen that is not immunogenic and not naturally expressed by the T lymphocytes. The T lymphocytes carrying either of these molecules can then be specifically destroyed by an antilymphocyte serum specific for the HLA molecules, or antibodies specifically directed against the said antigens. The "molecule allowing the specific destruction" of the T lymphocytes may also be a molecule encoded by a "suicide gene". The term "suicide gene" refers to a gene encoding a molecule that is toxic for the cell expressing it, conditionally.

The "subject" or "patient" to be treated may be any mammal, preferably a human being. The human subject may be a child, an adult or an elder. In other embodiments, the subject is a non-human mammal, such as cats, dogs, horses.

The term "treating" or "treatment" means any improvement in the disease to which it refers. It includes preventing disease occurrence or relapse, alleviating at least one symptom, or reducing the severity or the development of the disease. In particular it includes reducing the risk, occurrence or severity of acute episodes (flares). The term "treating" or "treatment" encompasses reducing the progression of the disease. In particular the invention encompasses preventing or slowing down the progression of the disease. The term "treating" or "treatment" further encompasses prophylactic treatment, by reducing the risk or delaying the onset of the disease, especially in a subject who is asymptomatic but has been diagnosed as being "at risk".

Tregs and Teffs to Modify

The Tregs and Teffs that can be modified according to the present invention may be polyclonal cells or specific cells. By "specific" is meant that the Tregs or Teffs specifically recognize and bind an antigen involved in the pathophysiology of the target disease. Specific Tregs are preferred, especially when the disease to treat is an autoimmune disease. Specific Tregs or Teffs may be obtained by co-expressing IL-2 or IL-15 with a targeting molecule which renders the cells antigen specific or ligand specific, e.g. targeting a particular tissue type. Specific Tregs may also refer to a global specificity of a population of cells. This can be obtained for example by harvesting cells from a site that likely contains specific cells (i.e. TILs for cancer) or by culturing the cells under certain conditions such as stimulation with specific antigens or alloantigenes. This can be also achieved by expressing specific T cell receptors (TCRs), advantageously both the alpha and beta chains of a TCR with a known specificity, or by expressing any targeting moiety such as those that have been used for designing Chimaeric antigen receptor (CAR) T-cells.

Tregs and Teffs subsets of particular interest may be found among activated or memory cells that are classically defined as central memory T cells that are CD45RA−CD45RO+CCR7+CD62L+, effector memory T cells that are CD45RA−CD45RO+CCR7−CD62L−, or effector cells that are CD45RA+CD45RO−CCR7−CD62L−. Further Tregs and Teffs subsets of particular interest may be found in specific target tissue or their draining lymph nodes (i.e. pancreas or pancreatic lymph nodes), or in tumors.

The Tregs and Teffs that can be modified according to the present invention may be autologous, i.e. harvested from the patients to be treated, or allogeneic, i.e. they are obtained from another subject than the subject to treat. In a preferred embodiment, the Tregs and Teffs are of the same species as the subject to treat. Preferably they are human cells. The donor is thus preferably human, and may be a fetus, a newborn, a child, an adult. The Tregs or Teffs preparations are obtained for example from peripheral blood, the blood product of a lymphapheresis, peripheral lymph nodes, the spleen, the thymus, cord blood, and the like.

Genetic Modification of the T Lymphocytes

According to the invention Tregs or T cells are modified to stably express IL-2 or IL-15. Such stable expression can be achieved by integration of nucleotide sequences that encode IL-2 or IL-5, which constitute the transgene(s) to express into the genome of the cells. Methods for stable integration of transgenes are known in the art.

Integrative viral vectors may be employed, such as, without limitation, retroviruses (e.g. oncoretroviruses, spumaviruses or lentiviruses).

The expression "lentivirus" denotes a category of retroviruses particularly preferred for the present invention. Examples of lentiviruses include, but are not limited to human lentiviruses such as HIV (in particular HIV-1 or HIV-2), simian immunodeficiency virus (SIV), equine infectious anemia virus (EIAV), feline immunodeficiency virus (FIV), Caprine Arthritis Encephalitis Virus (CAEV) and the VISNA virus.

The IL-2 or IL-15 encoding polynucleotide to express is typically operably linked to regulatory expression elements such as a promoter. In the present invention, any promoter able to promote the expression of the target polynucleotide in a cell, in particular a mammalian cell (e.g. a human cell) is included within the scope of the present invention. Thus promoter is advantageously an exogenous promoter. Such exogenous promoter can include, for instance, elongation factor 1-a (EF1-a), CMV, SV40, beta globin and PGK.

In the present invention, the lentiviral particles used are advantageously replication-defective i.e., once the lentiviral particle has entered into a cell, it cannot replicate alone to form new particles. Thus, the genes encoding the viral proteins necessary for the replication of the virus are not present or are defective, in the lentiviral particles. Typically, such a defect may be due to a mutation and/or deletion of one or more viral structural and replication functions (e.g. the gag, pol and env genes) in the genetic material. Because of their deficiency in replication, the replication-defective lentiviral particles of the invention are obtainable by a transcomplementation system (vector/packaging system).

The lentiviral particles may be pseudotyped with the envelope protein of the lentivirus used to prepare the lentiviral particles, or alternatively with a heterologous envelope protein that is chosen with respect to the cells to be targeted. In a particular embodiment, these envelope proteins are amphotropic (wide host range). In a preferred embodiment, said lentiviral vector is pseudotyped with a VSV-G protein. The VSV-G glycoprotein may originate from different serotypes of vesiculoviruses. In another embodiment, said lentiviral particles are pseudotyped with a protein that can mediates infection of lymphocytes, chosen in the group consisting of the MuLV amphotropic envelope, the Mokola envelope, the EboZ envelope, the Ebola-Reston (EboR) envelope, the influenza-hemagglutinin (HA) envelope, the respiratory syncytial virus (RSV) F and G, the Venezuelan equine encephalitis, the Western equine encephalitis and rabies virus envelope proteins and CMV envelope proteins.

Examples of conditions of transduction enabling the lentiviral particles to enter in contact with host cells (producer cells or target cells) and the genetic material to be integrated, are well known in the art and described in the experimental section.

In addition to traditional gene transduction approaches, one may also employ Transcription Activator-Like Effector Nucleases (TALENs), Zinc Finger Nuclease (ZFNs) or Clustered Regularly Interspaced Short Palindromic Repeats (CRISPR)-associated endonuclease protein (Cas) system, as they can make double strand break and increase frequency of gene targeting.

Meganucleases may also be employed. These are sequence-specific endonucleases originating from a variety of single-celled organisms such as Archaea or archaebacteria, bacteria, phages, fungi, yeast, algae and some plant organelles.

The expression of IL-2 or IL-15 can be either constitutive or inducible.

In a first embodiment, the expression of the transgene is constitutive. Such constitutive expression may be achieved by a number of techniques, e.g. by placing the nucleic acid that encodes IL-2 or IL-15 under the control of a promoter with constitutive expression. The promoters can be chosen among those that drive high gene expression such as EF1a or CMV promoters or among those that drive low expression such as PGK.

In another embodiment, the expression of the transgene may be inducible, i.e. the transgene is expressed only in response to an external stimulation.

Example of inducible promoters may be:
- a tetracyclin regulated promoter: Some of the elements of the systems include a tetracycline repressor protein (TetR), a tetracycline operator sequence (tetO) and a tetracycline transactivator fusion protein (tTA), which is the fusion of TetR and a herpes simplex virus protein 16 (VP16) activation sequence;
- a steroid regulated promoter: Some of the elements of the systems include using the rat glucocorticoid receptor (GR); the human estrogen receptor (ER); ecdysone receptors derived from different moth species; or different entities covering promoters from the steroid/retinoid/thyroid receptor superfamily.
- a physically activated promoter such as promoters activated by heat, cold of light Giry-Laterrière et al, 2011, Hum Gene Ther., 22(10):1255-67 describe examples of lentiviral vectors for drug-inducible gene expression.

These Tregs and Teffs could be further genetically modified to express proteins that would change their specificity such as to control their targeting. This can be achieved by expressing specific TCRs (e.g. both the alpha and beta chain of a TrCR with a known specificity) or any targeting moieties such as those that have been used for designing CAR-T cells (see e.g. Oladapo Yeku and Renier Brentjens, Biochem. Soc. Trans. (2016) 44, 412-418). Chimaeric antigen receptor (CAR) T-cell constructs typically consist of a single chain variable fragment (scFv) directed against a known antigen.

They could also express a molecule allowing their specific destruction. In a specific embodiment, the T cells are modified so as to express a transgene encoding a molecule allowing the specific destruction of the said T cells.

Specifically, the transgene is a "suicide" gene. For example, it may be a gene which encodes a molecule capable of phosphorylating a nucleoside analogue to a monophosphate molecule, itself convertible by cellular enzymes to a triphosphate nucleotide that can be incorporated into nucleic acids during extension under the effect of polymerases, the effect being the interruption of chain extension. The said nucleotide analogue may be for example acyclovir or gancyclovir. The said molecule expressed by the "suicide" gene may be in particular thymidine kinase (TK) of the herpes simplex virus type 1. The herpes simplex virus 1 thymidine kinase (HSV1 TK) is capable, when it is present in a sufficient concentration in the cells in question, of phosphorylating nucleotide analogues, such as a acyclovir (9-((2-hydroxyethoxy)methyl]guanine) or gancyclovir (9 [1,3-dihydroxy-2-propoxymethyl]guanine), to monophosphate molecules which are themselves convertible by cellular enzymes to triphosphate nucleotides which can be incorporated into nucleic acids during extension under the effect of polymerases within the said cells, the effect being the interruption of chain extension and the cell death which follows. In case of any adverse reaction, the nucleotide analogue (for example gancyclovir) is then administered to the patient. The suicide gene could also be cytosine deaminase that converts the non toxic 5-fluorocytosine (5-FC) into the toxic 5-fluororouracile (5-FU), or it could be an inducible caspase-9 suicide gene.

Examples of transduction protocols are described in international patent application WO2009/053629.

The expression of IL-2 increases the suppressive function of Tregs. Tregs which express IL-2 will not only survive better but will also function better than Tregs which do not express IL-2. Other improvements of Tregs function can be achieved by co-expressing genes coding for suppressive cytokines such as IL10, TGFβ.

Cell Therapy

The Tregs and Teffs modified according to the present invention are useful in cell therapy.

In particular, it is described a method for treating an autoimmune disease or an inflammatory disease in a patient, which method comprises administering an effective amount of a composition comprising such Tregs.

The autoimmune disease or inflammatory disease may be selected, without limitation, from the group consisting of type I diabetes mellitus (T1 D), Crohn's disease, ulcerative colitis, myasthenia gravis, Graves' disease, Hashimoto's disease, Addison's disease and autoimmune gastritis and autoimmune hepatitis, rheumatoid disease including rheumatoid arthritis and spondyloarthritis, systemic lupus erythematosus, systemic sclerosis and variants, polymyositis and dermatomyositis, pernicious anemia, autoimmune thrombocytopenia, Sjogren's syndrome, multiple sclerosis, psoriasis and uveitis. One skilled in the art understands that the methods of the invention can be applied to these or other autoimmune diseases, as desired.

Treatment of allergies are also encompassed, including but not limited to asthma, food or skin allergies.

In another aspect, it is provided a method for preventing or reducing the risk of graft rejection or graft versus host disease (GVHD) in a patient, which method comprises administering said patient with Tregs modified as described herein.

Typically the patient may be in need of a hematopoietic stem cell transplantation. The patient may indeed suffer from any disease which may be treated by a transplantation of HSC. This may include in particular cancers, such as malignant haemopathies, as well as genetic diseases, diseases which affect the haematopoietic system and/or the immune system.

In a particular embodiment, the Tregs may be administered during the "conditioning" of the patient before transplantation of haematopoietic stem cells, such as an allotransplantation of haematopoetic stem cells, as disclosed in international patent application WO2009/053631.

Cellular therapies including formulations and methods of administration are known in the art and can be applied to the T-regulatory cells and vectors described herein. See, for example, in EP1153131.

In another embodiment, it is described a method for treating a cancer in a patient, which method comprises administering an effective amount of a composition comprising such modified Teffs.

The cancer may be a solid tumor or a malignant haemopathy.

Among the solid tumors, there may be mentioned lung, skin, kidney, bladder, bone, liver, pancreatic, ovarian, breast, uterine, prostate, colon, colorectal, and head and neck cancers, and the like.

Among the malignant haemopathies, there may be mentioned acute leukaemia, myelodysplasia, or the lymphoproliferative syndrome (such as chronic lymphoid leukaemia, myeloma, lymphoma), myelodysplasias, acute lymphoblastic leukaemias (ALL) and acute myeloblastic leukaemias (AML), lymphomas, or a myeloma.

The patient may in particular suffer from a tumor relapse, for example a malignant haemopathy relapse.

In still another aspect, it is provided a method for treating an infection in a patient, which method comprises administering an effective amount of a composition comprising such modified Teffs. The infection may be an infection by any pathogenic agent, e.g. a viral infection, such as HIV, HBV, HCV, as well as EBV or CMV.

Large quantities of modified T cells and Tregs useful for a variety of commercial and clinical applications. This includes, for example, at least 1000,000 cells. In certain embodiments, the cell preparations comprise at least $5 \times 10^9$ T cells.

To obtain the desired quantity, the Tregs and Teffs, once genetically modified, may be cultured in a suitable culture medium.

The composition of T cells is typically administered by intravenous route. The quantity of Tregs and Teffs to administer may depend on the age, weight and sex of the subject, and of the particular disease to treat. Examples of ranges are between 100,000 cells to 1 billion or more, preferably between 1 million to 1 billion or more T cells.

The below Examples illustrate the invention without limiting its scope.

EXAMPLES

Example 1: Design of a Lentivirus Vector Expressing IL-2

A lentivirus was used to introduce and express the IL-2 gene permanently and constitutively in human Tregs.

Figure 1:
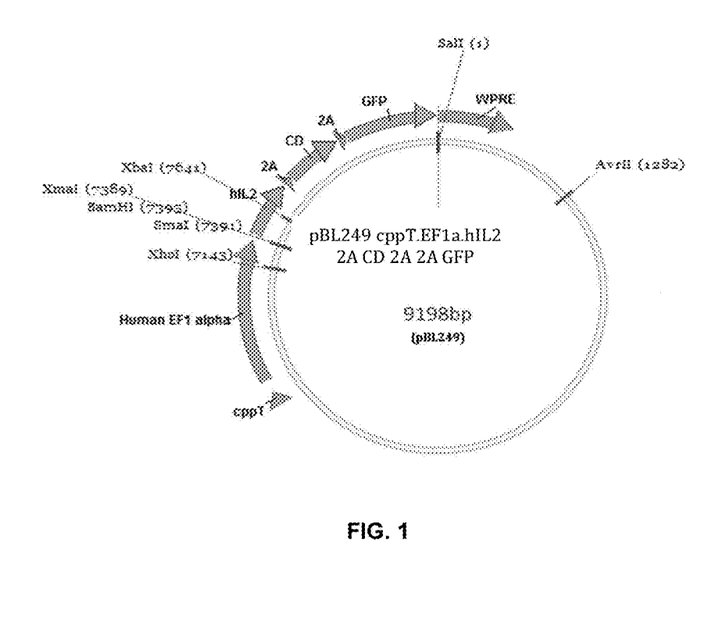

The map of the vector is shown as FIG. 1. For purpose linked to experimentation, a GFP transgene is incorporated such as to easily identify transduced cells. For clinical application, this GFP transgene could be either absent or substituted by any other transgene providing additional desired functionality (i.e. targeting or additional suppressive function).

Example 2: In Vitro Self-Sufficiency of Tregs Transduced with hIL2

Human Tregs were purified and transduced with the lentiviral vector described in Example 1, which encodes human IL-2 and GFP.

For that purpose, Tregs were purified from peripheral blood mononuclear cells (PBMCs) from healthy donors based on CD25 high expression using magnetic beads covered with anti-CD25 antibodies and MACS. Purity in CD3+CD4+CD25highCD127low Tregs is >90%. Tregs were then cultured at $0.5-1 \times 10^6$ cells/mL after activation by anti-CD3/anti-CD28 beads, in the presence of exogenous IL-2 (600 UI/mL) and rapamycine (100 nM) for 48 h. Cells were then washed and transduced with lentiviral supernatant at a MOI of 25. Cells were then cultured at 37° C. in incubators.

As a negative control, other human Tregs were infected with a vector encoding GFP alone (vector control) or used uninfected (NI). Tregs are cultured in vitro in a medium supplemented or not with exogenous IL-2 for 9 days to observe the IL-2 dependence of Tregs. The kinetic curves of expansion of Tregs are shown in FIGS. 2A, 2B.

Figure 2A:
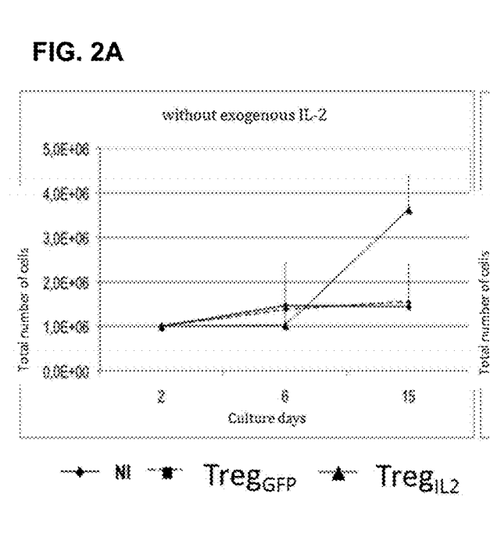
FIGS. 2A and 2B show kinetic curves of expansion of IL2-transduced or GFP-transduced Tregs versus non-transduced Tregs, cultured in the absence (FIG. 2A) or presence (FIG. 2B) of exogenous IL-2 (mean of three independent experiments). While all cells grow in the presence of exogenous IL-2, only the IL-2 transduced cells grow in its absence.
Figure 2B:
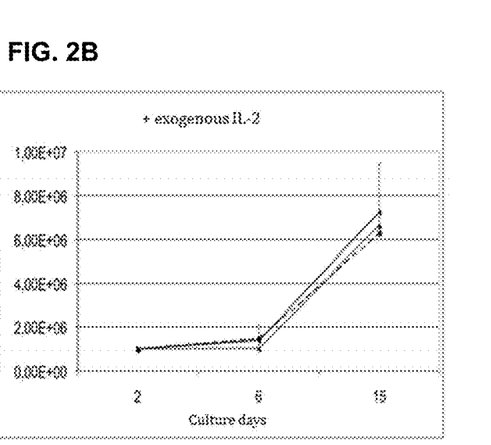

In the absence of exogenous IL-2, Tregs transduced with the gene coding for IL-2 (hIL-2-2A-GFP) proliferate between Day 6 and Day 15, while non-transduced Tregs (NI) or transduced with the GFP control vector did not proliferate (FIG. 2A). Transduced or control cells similarly proliferate in the presence of exogenous IL-2 (FIG. 2B).

Figure 2C:
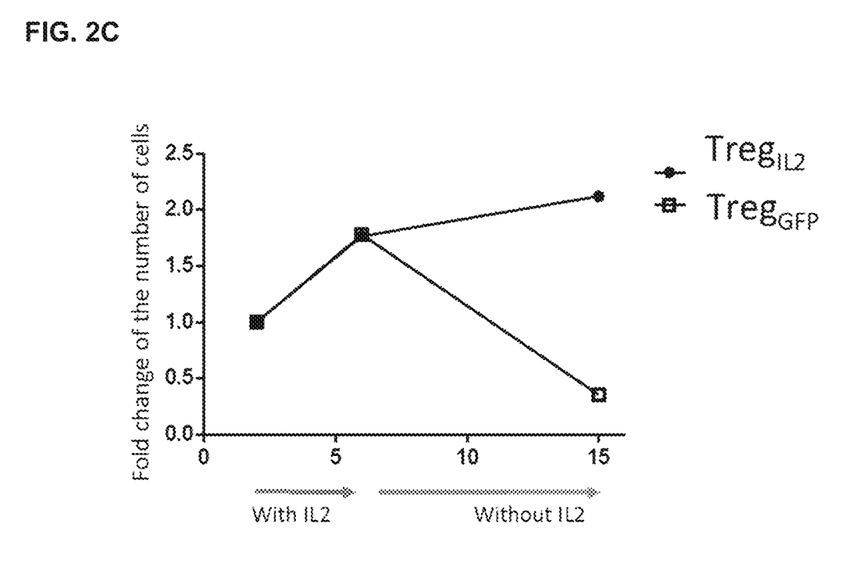
FIG. 2C shows kinetic curves of expansion of IL2-transduced or GFP-transduced Tregs, cultured for the first 6 days in the presence of exogenous IL-2, and then in its absence. While IL-2 transduced cells continue to grow in the absence of exogenous IL-2, the non-transduced cells stop growing and die.
Figure 2D:
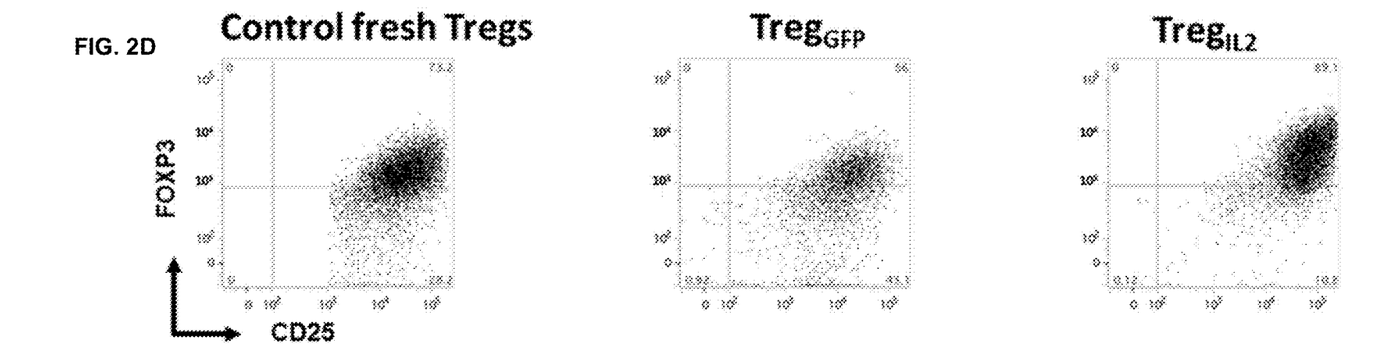
FIGS. 2D and 2E show expression of FoxP3, CD25 and phospho-STAT5 (pSTAT5) markers in cells that have been cultured like in FIG. 2C, after IL-2 withdrawal, and compared to fresh uncultured Tregs.
Figure 2E:
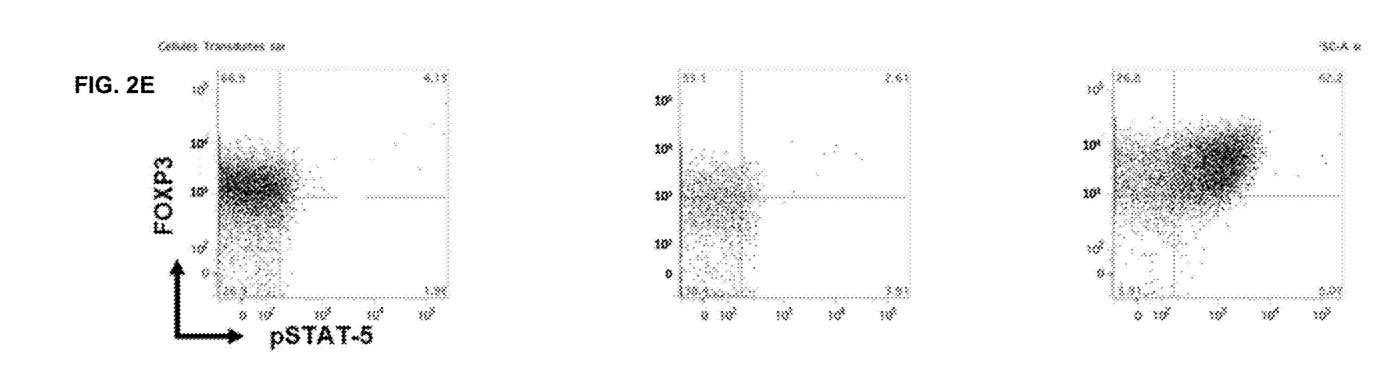

In a similar experiment, the cells are first all grown in the presence of IL-2 for 6 days, and then cultured without IL-2. While $Treg_{GFP}$ and $Treg_{IL2}$ grow similarly in the presence of exogenous IL2, only the $Treg_{IL2}$ continue to grow in its absence (FIG. 2C). These results show that Tregs transduced with the hIL-2 gene are self-supporting and expand in vitro. Phenotypic studies (FIGS. 2D-2E) further show that the $Treg_{IL2}$ are highly activated and suppressive. $Treg_{GFP}$ cultured without exogenous IL-2 express the same levels of CD25 and Foxp3 that control fresh Tregs, and they do not express pSTAT5. In contrast, $Treg_{IL2}$ express higher levels of CD25 and foxp3 than control fresh Tregs, and they also highly express pSTAT5 all indicating a highly activated status.

Figure 3A:
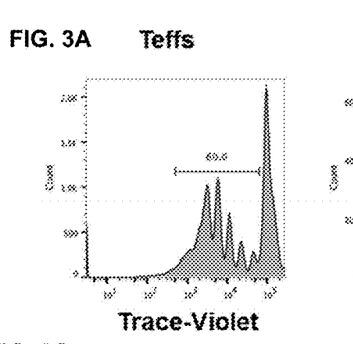
Figure 3B:
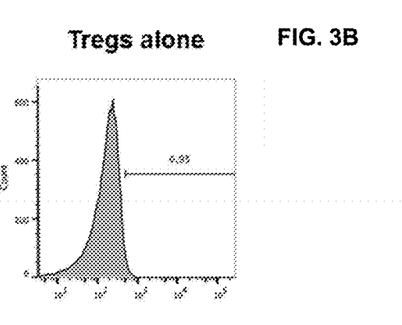
Figure 3C:
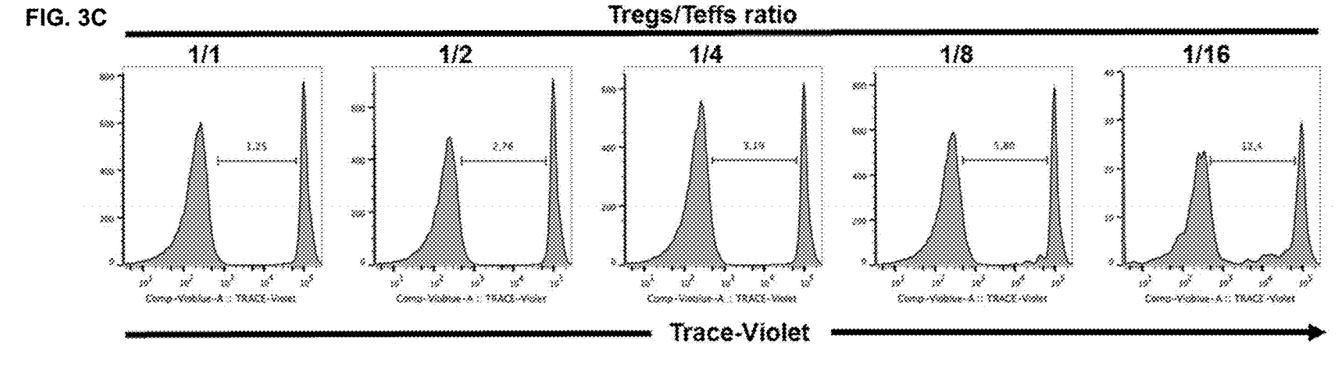

This high suppressive activity is shown in FIG. 3. Classical suppression assays for Tregs are performed by adding increasing amounts of Treg to Teffs that have been stained with a fluorescent dye that is progressively lost at each cell division. In the absence of Tregs, approximately 60% of the Teff have undergone division(s) as shown by the different peaks of less intensity (FIG. 3A). When adding Tregs, the Teff divisions are suppressed up to a ratio of 1/8 Treg/teff where approximately 6% of the Teff have undergone divisions(s), and approximately 12% of the Teff have undergone divisions(s) at a ratio of 1/16 (FIG. 3C).

Example 3: In Vivo Self-Sufficiency of Tregs Transduced with hIL2

Survival and self-sufficiency of Tregs transduced with hIL-2 were studied in vivo in immunodeficient NOD/SCID gamma c KO (NSG) mice.

The NSG mice are completely devoid of T, B and NK cells, and do not produce IL-2. This experimental model was chosen to validate the in vivo self-sufficiency of Tregs expressing IL-2.

Thus, Tregs transduced with the gene coding for IL-2 were transferred to NSG mice. The cells injected contained approximately 10% of GFP+ cells thus expressing IL-2, the rest being non-transduced cells.

The survival of all these cells was first monitored in peripheral blood (FIG. 4).

Figure 4A:
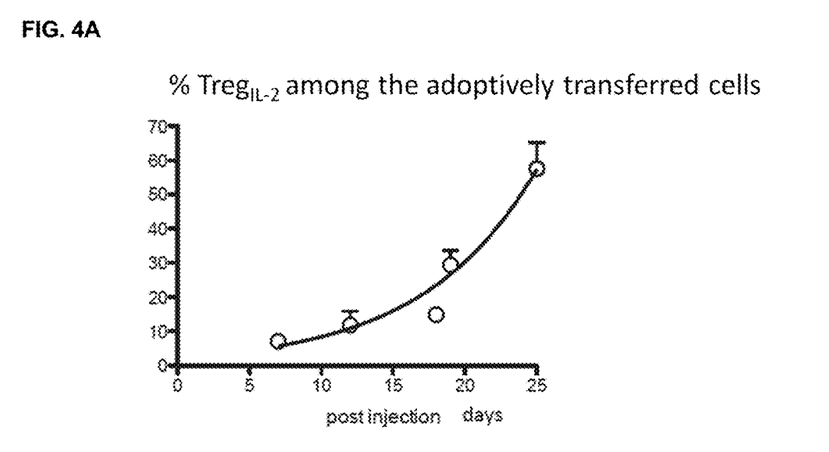
FIGS. 4A to 4C show the selective advantage survival of human Tregs transduced by the hIL-2-2A-GFP ($Treg_{IL2}$) vector adoptively transferred to recipient mice devoid of T cells in vivo. A population of human Tregs transduced by the hIL-2-2A-GFP are injected into mice lacking T cells. The proportion of transduced cells at the time of injection is approximately 8% of $Treg_{IL2}$. This proportion grows to 60% at day 25, illustrating the growth advantage of IL-2 producing Tregs (FIG. 4A).
Figure 4B:
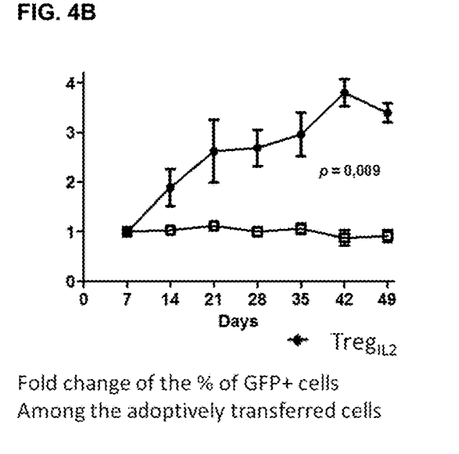
Figure 4C:
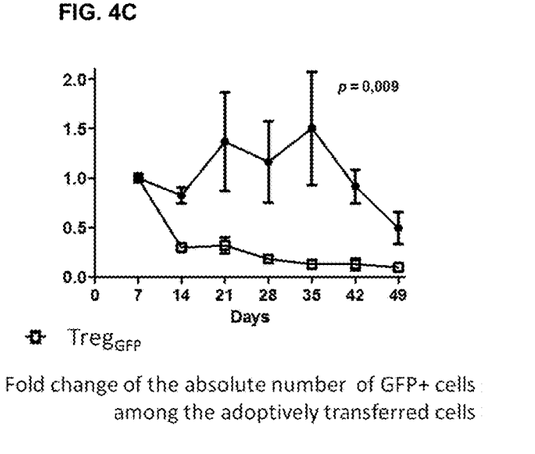

While when adoptively transferred at day 0 the T cells population transduced with the vector coding for IL-2 and GFP contained 10% transduced cells (i.e. that expressed GFP), this percentage of GFP increases continuously during the 25 day follow-up of the mice (FIG. 4A). In an independent experiment, the survival of TregIL2 and $Treg_{GFP}$ cells were compared. The percentage of transduced cells within the population of adoptively transferred cells remained stable for the Tregs transduced with GFP only, indicating that the GFP transduced cells have no growth/survival advantage over non transduced cells. In contrast, the percentage of transduced cells within the population of adoptively transferred cells increased progressively for the Tregs transduced with IL2 (+GFP), indicating that the IL2 transduced cells have a growth/survival advantage over non transduced cells (FIG. 4B). When the transduced adoptively transferred cells are enumerated, it shows that this number rapidly declines for the $Treg_{GFP}$, while it initially increases for $Treg_{IL2}$ (FIG. 4C).

Altogether, these results indicate that only Tregs expressing the hIL-2 gene are self-supporting and able to survive in vivo.

Figure 5A:
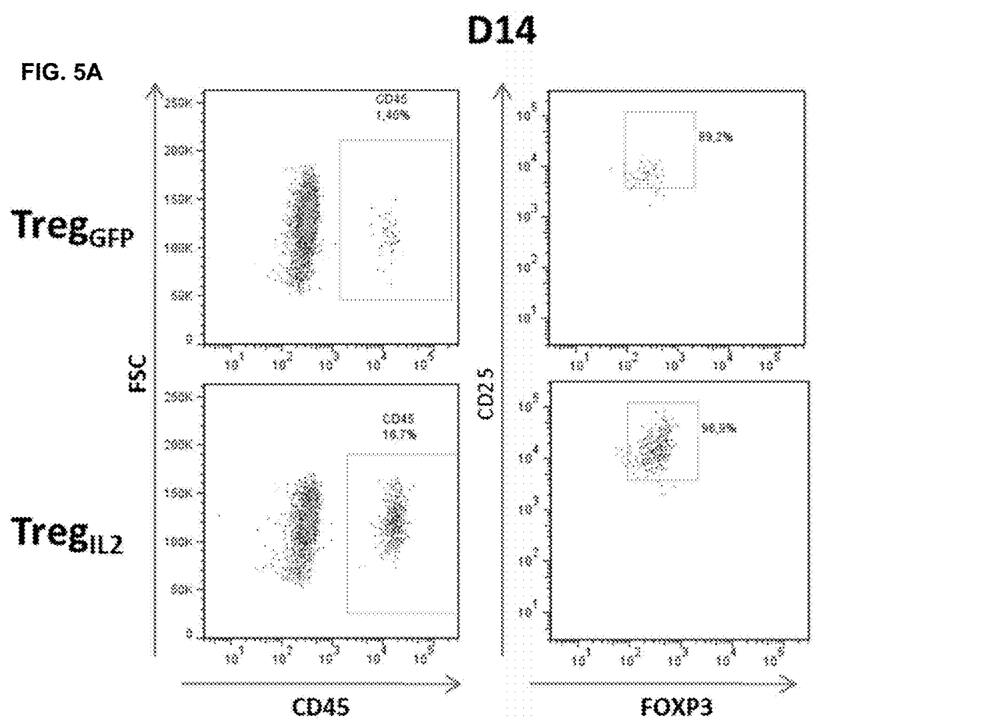

The phenotype of adoptively transferred cells shows that the TregIL2 are highly activated. At day 14 after transfer, there are many more surviving TregIL2 than $Treg_{GFP}$ (FIG.

Figure 5B:
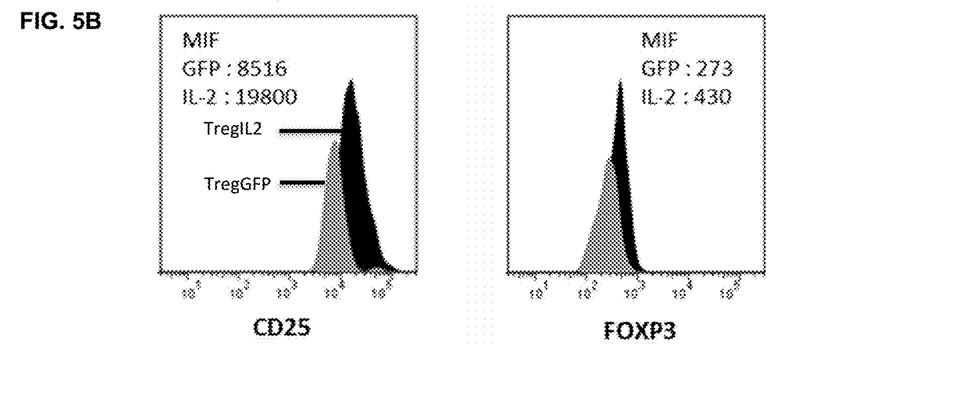
Figure 5C:
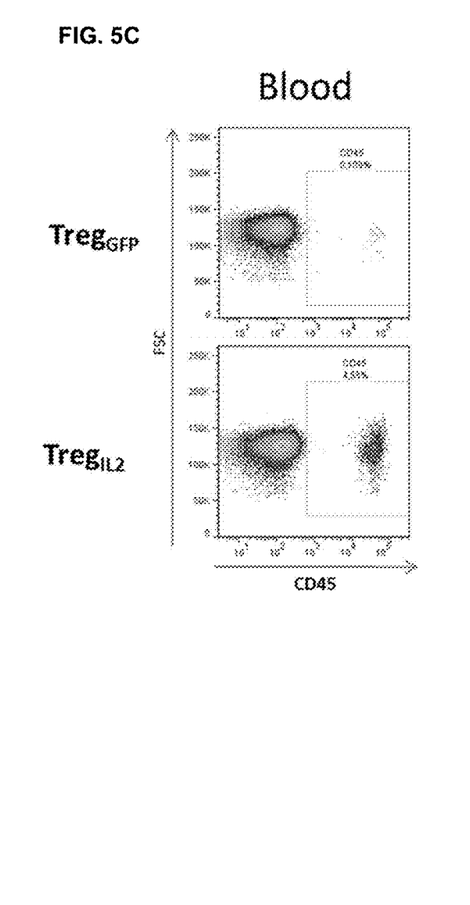
FIGS. 5C and 5D show the adoptively transferred cells at day 35, after the mice have been euthanized.
Figure 5D:
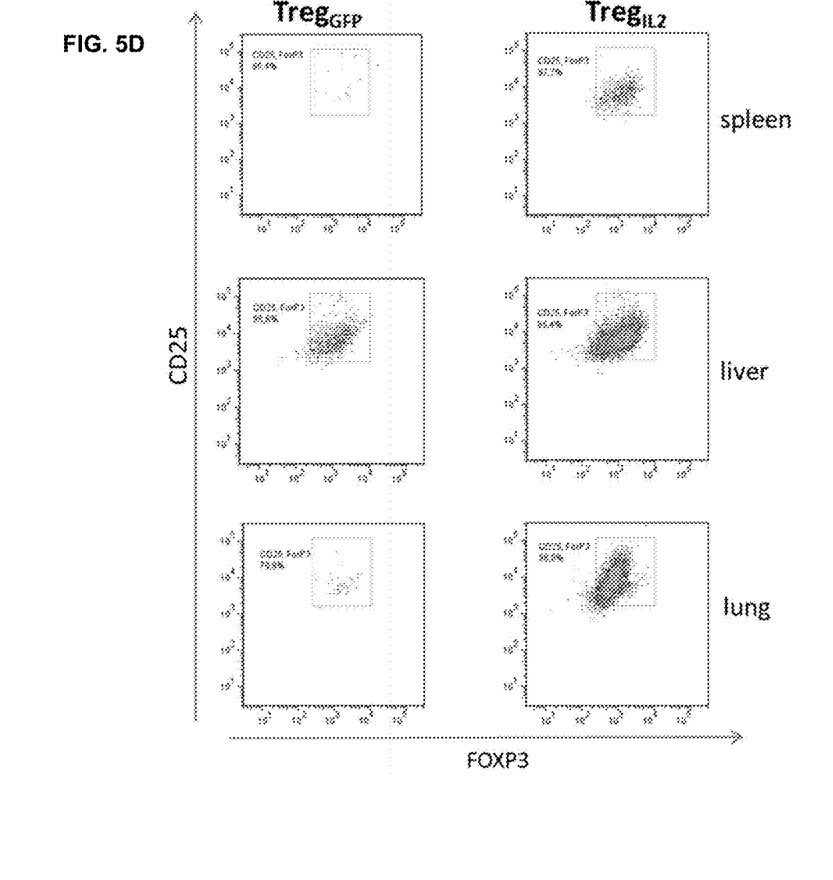

5A left panels) and they express higher levels of CD25 and of Foxp3 than the few surviving Treg$_{GFP}$ (FIG. 5A right panels & and FIG. 5B). The difference in the number of surviving cells is even more pronounced at day 35 (FIG. 5C), a time at which the mice are euthanized and the survival of adoptively transferred cells was monitored in tissues (FIG. 5D). Surviving Treg$_{GFP}$ could only be found in the liver, and they express low levels of CD25 and Foxp3. In contrast, many Treg$_{IL2}$ cells could be detected in spleen, liver and lungs emphasizing the survival advantage of Treg$_{IL2}$ that made them able to repopulate tissues. Noteworthy, these cells also highly express CD25 and Foxp3.

Figure 6:
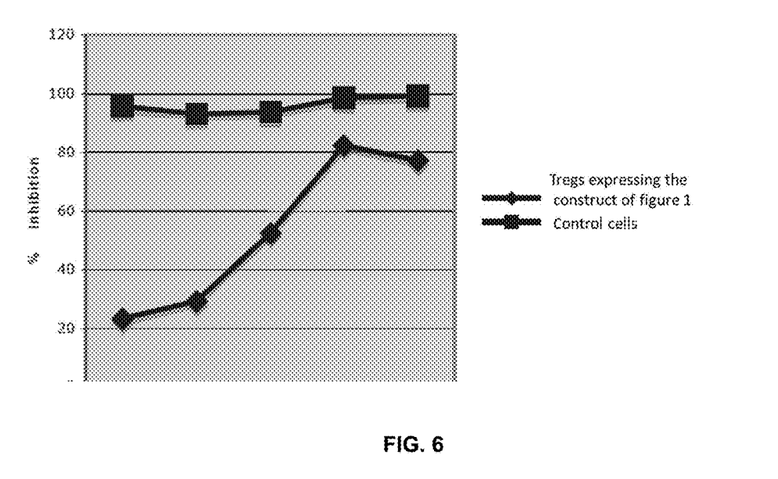
FIG. 6 is a graph that shows the efficiency of control of transduced cells expressing the cytosine deaminase suicide gene by 5-fluorocytosine (5-FC). Teffs transduced with the hIL-2-2A-CD-2A-GFP vector are purified for GFP expression by flow cytometry. These cells or untransduced control cells are cultured in the presence of increasing 5-FC concentration. Results show the percentage of inhibition of cell proliferation. These results indicate an inhibition greater than 98% of the proliferation of Teff cells expressing cytosine deaminase (CD) gene.

Example 4: Functionality of the Cytosine Deaminase (CD) Gene 5-fluorocytosine (5-FC) and 5-fluororouracile (5-FU) are two nucleoside analogs of cytosine. 5-FC is inactive, but is metabolized to 5-FU in the presence of cytosine deaminase (CD). 5-FU is then converted to 5-FU monophosphate (5-FU-MP) by uridine phosphoribosyl transferase (UPRT). 5FU-MP can be either be phosphorylated to 5-FC triphosphate and incorporated into RNA by inhibiting protein synthesis or it can be converted to 5-fluorodeoxyuridine monophosphate in the presence of UPRT which will inhibit the thymidylate synthetase essential in DNA synthesis. In order to validate the functionality of CD suicide gene, transduced T lymphocytes were purified based on GFP expression and then cultured in the presence of 5-FC for 4 days. Cell proliferation was determined by incorporation of tritiated thymidine (FIG. 6).

Example 5: Superior Functionality of Teff Transduced with hIL2

Figure 7A:
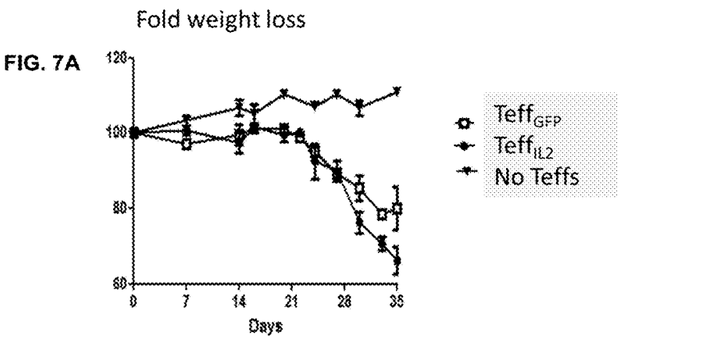
Figure 7B:
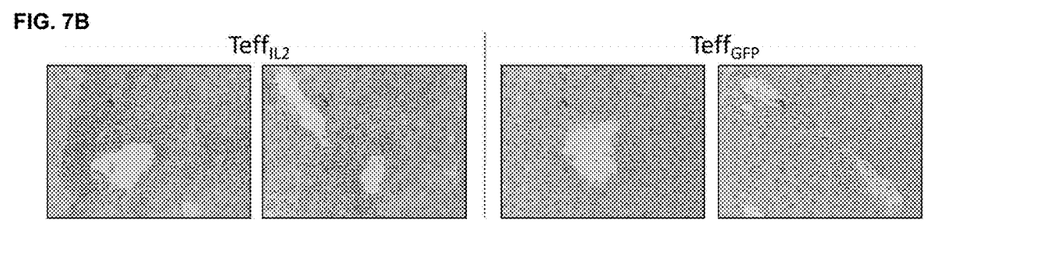

The efficiency of Teff expressing IL-2 (Teff$_{IL2}$) was evaluated in a model of experimental graft versus host disease (GVHD). NSG mice that lack T cells are adoptively transferred with Teff$_{GFP}$ or Teff$_{IL2}$. Weight loss and cellular infiltration of the liver are two main signs of GVHD that are analysed in this experiment. While control mice that have not received Teff gain weight, mice adoptively transferred with Teffs lost weight starting at 3 weeks. Mice that have received Teff$_{IL2}$ lost more weight than those having received Teff$_{GFP}$ (FIG. 7A). The T cell infiltration of the liver was much more pronounced for mice having received Teff$_{IL2}$ than those having received Teff$_{GFP}$ (FIG. 7B). Weight loss and liver cell infiltration indicate that the GVHD induced by Teff$_{IL2}$ is more pronounced than the one induced by Teff$_{GFP}$, likewise indicating the superior functionality of Teff$_{IL2}$ compared to Teff$_{GFP}$.

The invention claimed is:

1. A composition consisting essentially of human regulatory T (Treg) cells, wherein the Treg cells have been genetically modified to stably express a transgene encoding interleukin-2 (IL-2).

2. The composition of claim 1, wherein the cells have been genetically modified to stably express the IL-2 in a constitutive manner.

3. The composition of claim 1, wherein the cells have been genetically modified to stably express the IL-2 in an inducible manner.

4. The composition of claim 1, wherein the cells have been modified to further express a suicide gene, wherein the transgene and the suicide gene are integrated into the genome of the cells.

5. The composition of claim 1, wherein the cells have been modified by an integrative viral vector that comprises the transgene.

6. The composition of claim 1, wherein the cells have been modified by a system that allows integration of the transgene.

7. The composition of claim 1, wherein the cells are polyclonal cells.

8. The composition of claim 1, wherein the cells have been modified to co-express, with the IL-2, a targeting molecule that makes the cells antigen-specific or ligand-specific.

9. The composition of claim 1, wherein the interleukin-2 is des-alanyl-1, serine 125 human interleukin-2.

10. The composition of claim 1, wherein the interleukin-2 contains an amino acid substitution selected from the group consisting of N88R, N88I, N88G, D20H, D109C, Q126L, Q126F, D84G, and D84I relative to human mature IL2 protein comprising the amino acid sequence of SEQ ID NO: 3.

11. A method for reducing or alleviating at least one symptom of an autoimmune disease or an inflammatory disease in a human patient, the method comprising administering to said patient an effective amount of the composition of claim 1.

12. A method for reducing the risk of graft rejection or graft versus host disease (GVHD) in a human patient, the method comprising administering to said patient an effective amount of the composition of claim 1.

13. The method of claim 11, wherein the cells are autologous to the patient.

14. The composition of claim 5, wherein the integrative viral vector is a lentivirus vector.

15. The composition of claim 6, wherein the system that allows integration of transgenes is Crspr-Cas9 system, Zinc finger nucleases, TALENs or meganucleases.

16. The method of claim 14, wherein the cells are autologous to the patient.

17. The method of claim 11, wherein the cells are allogeneic to the patient.

18. The method of claim 14, wherein the cells are allogeneic to the patient.

19. The composition of claim 1, wherein the purity of the Treg cells in the composition is at least 90%.

* * * * *